(12) United States Patent
Oishi

(10) Patent No.: US 8,797,111 B2
(45) Date of Patent: Aug. 5, 2014

(54) POLY-PHASE FILTER, AND A SINGLE-SIDE BAND MIXER INCLUDING THE SAME

(75) Inventor: Kazuaki Oishi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 279 days.

(21) Appl. No.: 13/333,471

(22) Filed: Dec. 21, 2011

(65) Prior Publication Data

US 2012/0092085 A1   Apr. 19, 2012

Related U.S. Application Data

(63) Continuation of application No. PCT/JP2009/003131, filed on Jul. 6, 2009.

(30) Foreign Application Priority Data

Jun. 26, 2009   (EP) ..................................... 09163878

(51) Int. Cl.
*H04L 27/20*   (2006.01)

(52) U.S. Cl.
USPC ........... 332/103; 455/209; 455/323; 455/326; 327/552

(58) Field of Classification Search
USPC .................. 455/209, 323, 326; 327/238, 552; 332/103
See application file for complete search history.

(56) References Cited

U.S. PATENT DOCUMENTS

| | | |
|---|---|---|
| 2004/0116096 A1 | 6/2004 | Shen |
| 2005/0245225 A1 | 11/2005 | Park et al. |
| 2006/0068740 A1 | 3/2006 | Yokoyama |
| 2006/0246861 A1 | 11/2006 | Dosanjh et al. |
| 2007/0155350 A1 | 7/2007 | Razavi et al. |
| 2008/0132189 A1* | 6/2008 | Maxim et al. ................. 455/280 |
| 2010/0178890 A1 | 7/2010 | Fujii et al. |
| 2011/0068843 A1* | 3/2011 | Kodama ....................... 327/238 |

FOREIGN PATENT DOCUMENTS

| | | |
|---|---|---|
| CN | 1684357 A | 10/2005 |
| CN | 1723610 A | 1/2006 |
| CN | 101197531 A | 6/2008 |
| JP | 05-122008 A | 5/1993 |
| JP | 2001-045080 A | 2/2001 |
| JP | 3492560 B2 | 2/2004 |
| JP | 2006-121665 A | 5/2006 |
| WO | WO 2008/126360 A1 | 10/2008 |

OTHER PUBLICATIONS

Chinese Office Action with Search Report, Chinese Patent Application No. 200980160332.3 issued Dec. 4, 2013.

Thomas H. Lee et al., "The Design of CMOS Radio-Frequency Integrated Circuits", Cambridge University Press Second Edition, pp. 705-706.

* cited by examiner

*Primary Examiner* — Robert Pascal
*Assistant Examiner* — Jeffrey Shin
(74) *Attorney, Agent, or Firm* — Arent Fox LLP

(57) ABSTRACT

A 4-phase filter includes four filter units including resistors and capacitors which inputs input signals, and provides the input signal via a switch buffer to a secondary capacitor provided in parallel to a primary capacitance of each filter unit, thus enabling a shift of an operational frequency band according to whether or not the switch buffer is in an output-high-impedance state.

13 Claims, 18 Drawing Sheets

FIG. 6

ROUTE OF Rt1:

$$\cos(wlo1t) \cdot \cos(wlo2t) = \frac{e^{jwlo1t} + e^{-jwlo1t}}{2} \cdot \frac{e^{jwlo2t} + e^{-jwlo2t}}{2} \quad \cdots (1)$$

$$= \frac{1}{4} \cdot (e^{j(wlo1t+wlo2t)} + e^{j(wlo1t-wlo2t)} + e^{(-jwlo1t+jwlo2t)} + e^{(-jwlo1t-jwlo2t)}) \quad \cdots (2)$$

ROUTE OF Rt3:

$$\sin(wlo1t) \cdot \sin(wlo2t) = \frac{e^{j(wlo1t)} - e^{-(jwlo1t)}}{2} \cdot \frac{e^{j(wlo2t)} - e^{-j(wlo2t)}}{2} \quad \cdots (3)$$

$$= \frac{1}{4} \cdot (e^{j(wlo1t+wlo2t)} - e^{j(wlo1t-wlo2t)} - e^{(-jwlo1t+jwlo2t)} + e^{-j(wlo1t+wlo2t)})$$

Rt1+Rt3:

$$= \frac{1}{2} \cdot (e^{j(wlo1t+wlo2t)} + e^{-j(wlo1t+wlo2t)}) = \cos(wlo1+wlo2)$$

$$I = RF \cdot \cos(wlo1t+wlo2t) \quad \cdots (4)$$

$$Q = RF \cdot \sin(wlo1t+wlo2t) \quad \cdots (5)$$

POLY-PHASE FILTER, AND A SINGLE-SIDE BAND MIXER INCLUDING THE SAME

CROSS REFERENCE TO RELATED APPLICATION

This application is a continuation of International Application No. PCT/JP2009/3131, filed on Jul. 6, 2009, now pending, herein incorporated by reference.

FIELD OF THE INVENTION

The present embodiment relates to a poly-phase filter and a single-side band mixer including the same.

BACKGROUND OF THE INVENTION

A reception device of a communication system includes a reception circuit which downconverts a high-frequency signal received by an antenna and demodulates the downconverted signal. On the other hand, a transmission device of a communication system includes a transmission circuit which modulates transmission data and upconverts the same into a high-frequency signal.

For example, a reception circuit includes a downconverting mixer which downconverts a received high-frequency signal by a first local frequency, and a quadrature-demodulating mixer which quadrature-demodulates the downconverted signal by second local frequencies having phases shifted from each other. Also, a transmission circuit includes a quadrature-modulating mixer which quadrature-modulates transmission data by third local frequencies having phases shifted from each other, and a upconverting mixer which upconverts the quadrature-modulated signal by a fourth local frequency.

A single-side band mixer uses 4-phase local signals having phases shifted from one another by 90 degrees, as the above described local frequency signals of the upconverting mixer and the downconverting mixer. Then, the reception circuit using them is enabled to eliminate a spurious signal existing on the opposite side of the first local frequency from the received high-frequency signal, and, on the other hand, the transmission circuit is enabled to eliminate a spurious signal existing on the opposite side of the fourth local frequency from the high-frequency signal to be transmitted. As such the mixer for eliminating the spurious signals, a single-side band mixer is used.

As a local-signal generating circuit for generating 4-phase local signals, a poly-phase filter is used. As for a poly-phase filter, for example, there are descriptions in Patent Document, Japanese patent laid-open publications No. 2006-121665 (FIG. 10), or in Non-Patent Document, "The Design of CMOS Radio-Frequency Integrated Circuits, SECOND EDITION" (Thomas H. Lee, Pages 705-706, FIGS. 19.8, 19.9). A poly-phase filter generates, from a high-frequency input signal 4-phase high-frequency output signals having phases shifted by 90 degrees from one another. Here, the phase accuracy of the high-frequency output signals is restricted by a cut-off frequency band of the filter.

Patent Document, Japanese patent laid-open publications No. 2006-121665 (FIG. 10)
Non-Patent Document, "The Design of CMOS Radio-Frequency Integrated Circuits, SECOND EDITION" (Thomas H. Lee, Pages 705-706, FIGS. 19.8, 19.9)

SUMMARY OF THE INVENTION

According to an embodiment, a poly-phase filter inputting an input signal and outputting first-fourth 4-phase output signals, includes: first-fourth resistors, each of which has an input terminal and an output terminal; a first primary capacitor provided between the output terminal of the first resistor and the input terminal of the fourth resistor; a second primary capacitor provided between the output terminal of the second resistor and the input terminal of the first resistor; a third primary capacitor provided between the output terminal of the third resistor and the input terminal of the second resistor; a fourth primary capacitor provided between the output terminal of the fourth resistor and the input terminal of the third resistor; an input buffer which inputs and outputs to the input terminals of the first-fourth resistors the input signal; a first secondary capacitor which is connected to the output terminal of the first resistor in parallel to the first primary capacitor; a first switch buffer which inputs and outputs to the first secondary capacitor the input signal being input to the input terminal of the fourth resistor; a second secondary capacitor which is connected to the output terminal of the second resistor in parallel to the second primary capacitor; a second switch buffer which inputs and outputs to the second secondary capacitor the input signal being input to the input terminal of the first resistor; a third secondary capacitor which is connected to the output terminal of the third resistor in parallel to the third primary capacitor; a third switch buffer which inputs and outputs to the third secondary capacitor the input signal being input to the input terminal of the second resistor; a fourth secondary capacitor which is connected to the output terminal of the fourth resistor in parallel to the fourth primary capacitor; and a fourth switch buffer which inputs and outputs to the fourth secondary capacitor the input signal being input to the input terminal of the third resistor, wherein the first-fourth output signals are respectively output from the output terminals of the first-fourth resistors, and the first-fourth switch buffers are controlled, in response to a switching signal, to be either output-high-impedance state or not.

The second aspect of an embodiment relates to a single-side band mixer including a poly-phase filter.

BRIEF DESCRIPTION OF DRAWINGS

FIG. 6 illustrates multiplication computations by a mixer of the single-side mixers in FIG. 5.

DESCRIPTION OF THE EMBODIMENTS

Hereafter, with reference to drawings, embodiments of a poly-phase filter and a single-side band mixer having the same will be explained.

Figure 1:
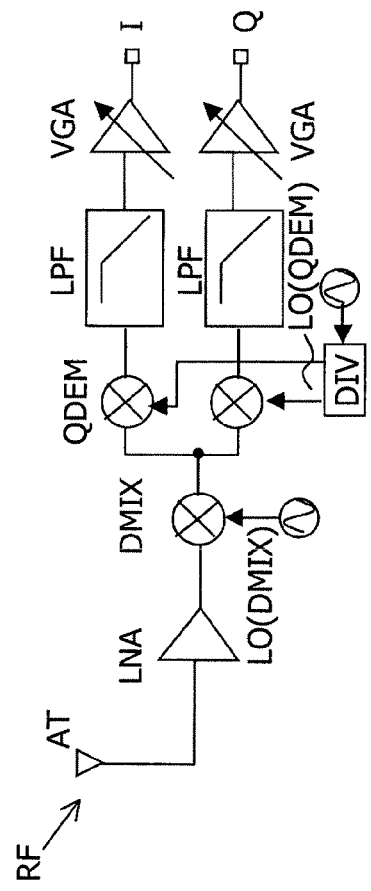
FIG. 1 is a configuration drawing of a reception circuit for a communication system.

FIG. 1 is a configuration drawing of a reception circuit of a communication system. This reception circuit includes an antenna AT which receives a radio-transmitted high-frequency input signal RF, a low-noise amplifier LNA which amplifies the received high-frequency signal RF, a downconverting mixer DMIX which multiplies the amplified high-frequency signal by a first local frequency signal LO(DMIX), a quadrature-demodulating circuit QDEM having two mixers which multiply the output of the downconverting mixer DMIX by each of second local frequency signals LO(QDEM) having phases shifted by π/2 from each other, low-pass filters LPF which eliminate high-frequency components from the outputs of the mixers, and variable gain amplifiers VGA which amplify the outputs thereof, outputting I signal and Q signal of the baseband.

When the reception circuit processes a differential signal, the first local frequency signal LO(DMIX) includes 2-phase local signals, and the second local frequency signal LO(QDEM) includes 4-phase local signals.

Figure 2:
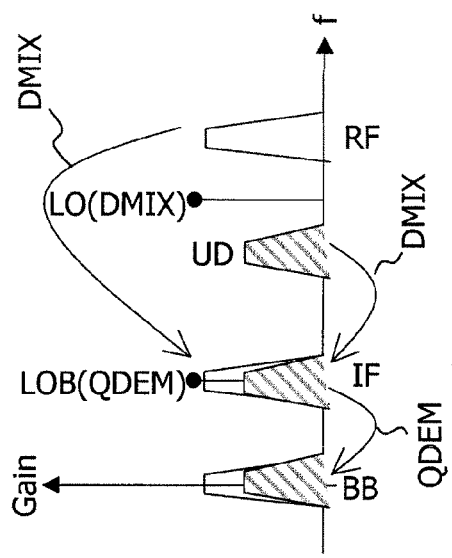
FIG. 2 illustrates frequencies of signals of the reception circuit in FIG. 1.

FIG. 2 is a drawing for illustrating frequencies of signals of the reception circuit of FIG. 1. The received high-frequency signal RF is downconverted by the downconverting mixer DMIX into an intermediate-frequency signal having an intermediate frequency IF corresponding to the frequency difference between the high-frequency signal RF and the first local frequency signal LO(DMIX), and further downconverted by the quadrature-demodulating circuits QDEM into signals of the baseband BB.

Here, a spurious signal UD existing on the opposite side of the first local frequency signal LO(DMIX) from the high-frequency signal RF is similarly downconverted into the intermediate frequency IF, and further into signals of the baseband BB. Therefore, within the I, Q baseband signals, components of the spurious signal UD are included, thus deteriorating the reception quality.

Figures 3, 4:
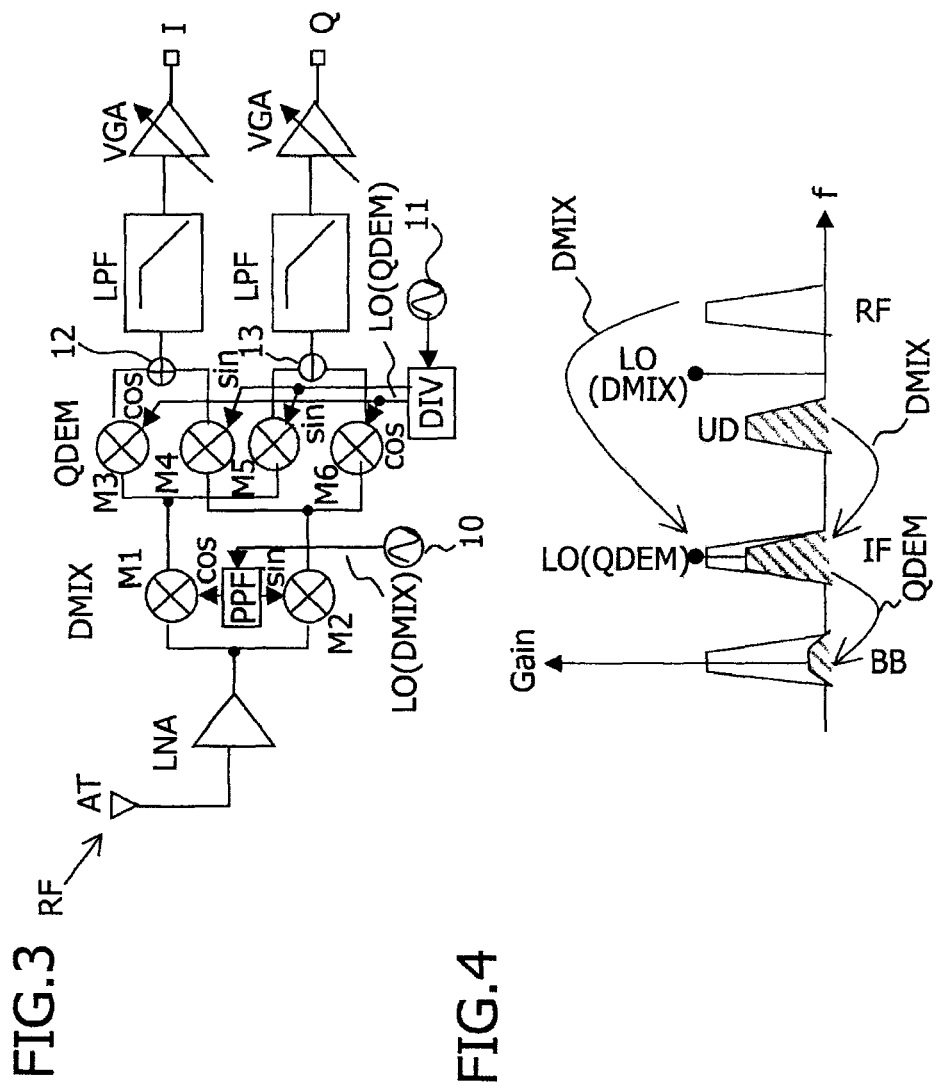
FIG. 3 is a configuration drawing of a reception circuit with single-side band mixers.
FIG. 4 illustrates frequencies of signals of the reception circuit in FIG. 3.

FIG. 3 is a configuration drawing of the reception circuit with single-side band mixers. In this reception circuit, a down mixer DMIX includes a poly-phase filter PPF, which takes in the first local frequency signal LO(DMIX) generated by the oscillator 10 and generates 4-phase (shifted by π/2 from one another) local signals, and two mixers M1, M2, each of which multiplies the received high-frequency signal by the first local frequency signal having phases shifted by π/2 generated by the poly-phase filter PPF. Further, the quadrature-demodulating circuit QDEM includes a divider DIV, which divides with a ratio of 1/2 the second frequency signal generated by the oscillator 11, four mixers M3-M6, which multiply the 4-phase second frequency signals LO(DEM) generated by the divider DIV by the intermediate frequency signals output from the mixers M1, M2, an adder 12, and a subtractor 13.

The output of the adder 12 turns, via the low pass filter LPF and the variable gain amplifier VGA, into the I signal, and, on the other hand, the output of the subtractor 13 turns, via the low pass filter LPF and the variable gain amplifier VGA, into the Q signal.

In FIG. 3, as a multiplication signal to each mixer, a cosine signal and a sine signal are illustrated. Here, when the reception circuit processes the differential signal, the positive-phase signals are multiplied by +cos and +sin, and the opposite-phase (or, the negative-phase) signals are multiplied by −cos and −sin. Hence, both of the first and the second local frequency signals are 4-phase signals.

FIG. 4 is a drawing for illustrating frequencies of signals of the reception circuit of FIG. 3. Similarly to FIG. 2, by the downconverting mixer DMIX, a spurious signal UD is downconverted, together with the received high-frequency signal RF, into the intermediate frequency IF. In the quadrature-demodulating circuit QDEM, however, the components of the spurious signal UD are eliminated, and the components of the high-frequency signal RF are selectively frequency-converted into the baseband BB. That is, it is enabled to selectively downconvert the single-side signal RF of the first local frequency LO (QDEM). The reason for the above is briefly explained as follows.

Figure 5:
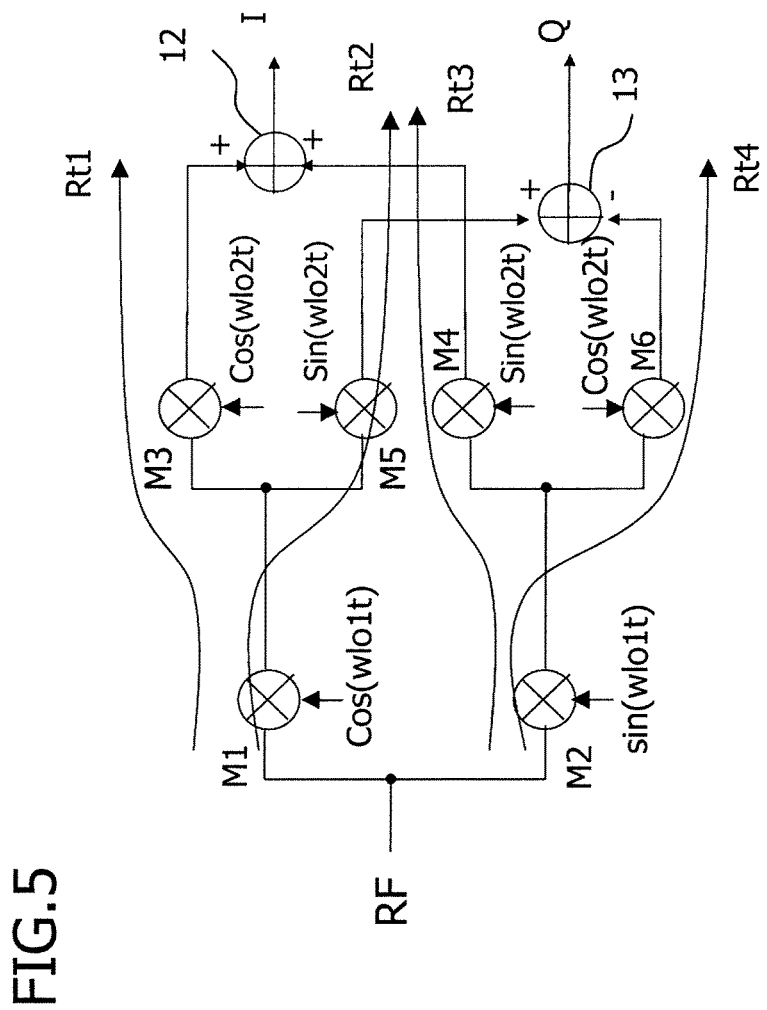
FIG. 5 illustrates configurations of single-side band mixers and local frequency signals each input into the mixers.

FIG. 5 is a drawing for illustrating the configuration of a single-side band mixer and the local frequency signal input into each mixer. In FIG. 5, similarly to FIG. 3, the mixers M1-M6, the adder 12, and the subtractor 13 are illustrated. Here, only the positive-phase side of the differential circuit is illustrated, while the opposite-phase side has the same circuit configuration.

For the angular frequency of the first local frequency signal LO(DMIX) being wlo1, and the angular frequency of the second local frequency signal LO(DMIX) being wlo2, cos(wlo1$t$), sin(wlo1$t$), cos(wlo2$t$), and sin(wlo2$t$) are respectively provided to each of the mixers M1-M6, as illustrated, and multiplied to the reception signal RF.

FIG. 6 is a drawing for illustrating the multiplication computation of the single-side mixer of FIG. 5. On a route Rt1 in FIG. 5, to the input high-frequency signal RF, the first local frequency signal cos(wlo1$t$) is multiplied by the mixer M1, and the second local frequency signal cos(wlo2$t$) is multiplied by the mixer M3. Therefore, these signals cos(wlo1$t$), cos(wlo2$t$) being multiplied are such as described by Formula (1) in FIG. 6.

Similarly, on a route Rt3 in FIG. 5, to the high-frequency signal RF, the first local frequency signal sin(wlo1$t$) is multiplied by the mixer M2, and the second local frequency signal sin(wlo2$t$) is multiplied by the mixer M3. These signals sin(wlo1$t$), sin(wlo2$t$) being multiplied are represented by Formula (2) as in FIG. 6.

Then, by the adder 12, Formulas (1), (2) are added to obtain Formula (3). Therefore, the I signal is represented by Formula (4), such that I=RF*cos(wlo1$t$+wlo2$t$).

Here, the angular frequency wlo1$t$ corresponds to a frequency of the first local frequency signal LO(DMIX), and the angular frequency wlo2$t$ corresponds to both a frequency of the second local frequency LO(QDEM) and a frequency difference between RF and LO(QDIM). That is, LO(QDEM)=RF−LO(QDIM) therefore RF=LO(QDIM)+LO(QDEM). Therefrom, the angular frequency (wlo1$t$+wlo2$t$) described in the above formula corresponds to a frequency of the high-frequency signal RF. Therefore, in FIG. 4, if the input high-frequency signal RF being multiplied by cos(wlo1$t$+wlo2$t$), the input high-frequency signal RF is selectively downconverted into the baseband BB, while the spurious signal UD is not downconverted into the baseband BB. That is, the spurious signal UD is eliminated.

The Q signal generated on routes Rt2 and Rt4 in FIG. 5 is represented, similarly to the above, by Formula (5) in FIG. 6, such that Q=RF*sin(wlo1$t$+wlo2$t$). Therefore, as for the Q signal, the input high-frequency signal RF is selectively downconverted into the baseband BB, while the spurious signal UD is not downconverted into the baseband BB, thus being eliminated.

As the above, the single-side band mixer is enabled to eliminate, in the reception circuit, the spurious signal UD which is an image signal against the high-frequency signal RF to be received. Also, in an application to a transmission circuit, it is enabled to eliminate the spurious signal UD, and to selectively generate the high-frequency signal as an output signal.

As described above, since the first local frequency signal LO(DMIX) has a higher frequency compared with the second local frequency signal LO(QDEM), the poly-phase filter PPF is used for generating 4-phase signals instead of a divider.

Figure 7:
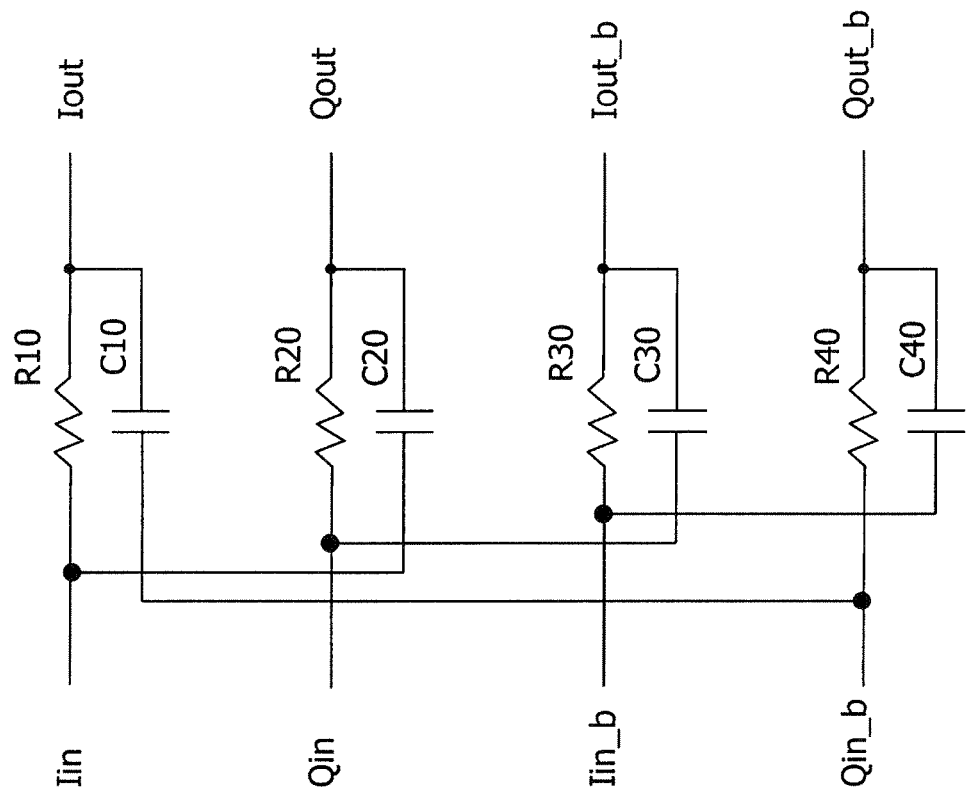
FIG. 7 is a circuit diagram of a poly-phase filter.

FIG. 7 is a circuit diagram of a poly-phase filter. The poly-phase filter, configured to have in parallel four RC-filter units including resistors R10-R40 and capacitors C10-C40, take 4-phase input signals Iin, Qin, Iin_b, and Qin_b into input terminals (left-side terminals) of the resistors R10-R40, and outputs the 4-phase output signals Iout, Qout, Iout_b, and Qout_b from output terminals (right-side terminals) thereof. The Iin_b is a opposite-phase (phase being shifted by $\pi$) signal to the Iin, and the Qin_b is a opposite-phase signal to the Qin. Also, the phases of the Iin and the Qin are shifted by $\pi/2$ from each other. The output signals are the same. Further, the capacitors C10-C40 are respectively connected to the input sides of the resistors R40, R10, R20, and R30, and thereby four filter units are connected in a clockwise (or counter-clockwise) fashion. The resistors R10-R40 have the same resistance values, and the capacitors C10-C40 have the same capacitance values.

The accuracy of the phase relations of the 4-phase input signals is low, but if the 4-phase input signals pass through the poly-phase filter, the accuracy of a the phase relations thereof will be improved. The reason for it is because, as described in Non-patent Document mentioned above, the RC filter is assumed to be as a low pass filter or a high-pass filter. Since, at such the filters, phases are shifted by 90 degrees ($\pi/2$) at the cut-off frequency band, by connecting the four RC-filter units in a clockwise fashion, the 4-phase output signals having phases shifted from one another by 90 degrees ($\pi/2$) with high-accuracy are generated at the right-side terminals of the resistors R, which are outputs of the RC filters. Here, the frequency band, at which phase relation of 90 degrees is established with high accuracy, is the cut-off frequency Fc of the RC filter, such that Fc=1/(2$\pi$RC).

That is, the poly-phase filter PPF generates the 4-phase first local frequency signals LO(DMIX) only at around cut-off frequencies Fc of the four filter units, which constitute the poly-phase filter.

From the above, input signals are not necessarily 4-phase input signals, butt-phase input signals Iin and Iin_b may be respectively input into the resistors R10, R20 and the resistors R30, R40. Also, a single-phase input signal may be input to all of the resistors R10-R40. For example, by providing the poly-phase filter unit as illustrated in FIG. 7 in multiple stages, the phase relations of the four output signals are gradually formed such that the phases are shifted by 90 degrees from one another with high accuracy. Excessive number of stages, however, are not preferred, because the signal attenuates as passing the stages.

Figure 8:
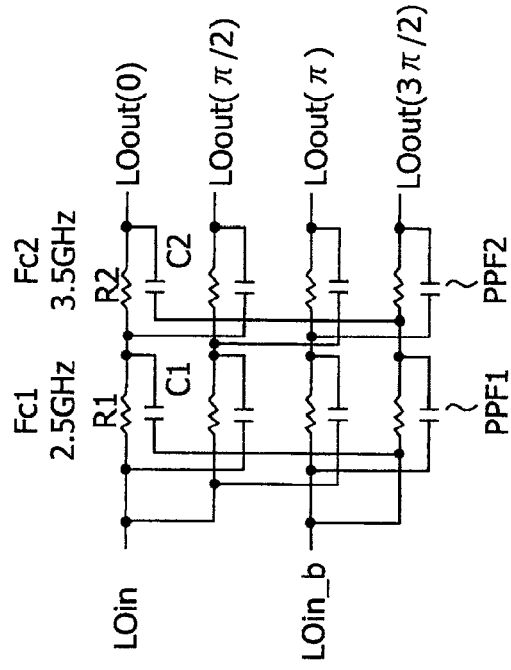
FIG. 8 is a configuration drawing of a 2-stage poly-phase filter.

FIG. 8 is a configuration drawing of a 2-stages (2-order) poly-phase filter. This example includes a first stage poly-phase filter PPF1 and a second stage poly-phase filter PPF2. To the first stage poly-phase filter PPF1, 2-phase input signals LOin, LOin_b are input. Also, four outputs from the first stage are connected to four inputs of the second stage, and 4-phase output signals LOout(0)-LOout(3$\pi$/2) are output from four output terminals of the second stage. At the first stage, the filter is all constituted by the resistor R1 and the capacitor C1, and, at the second stage, the filter is all constituted by the resistor R2 and the capacitor C2.

Here, the cut-off frequency Fc1 by the first stage resistor R1 and capacitor C1 is set to be 2.5 GHz, and the cut-off frequency Fc2 by the second resistor R2 and capacitor C2 is set to be 3.5 GHz. Thereby, the first stage filter PPF1 generates high-accuracy 4-phase signals within a frequency band, Fc1=2.5 GHz, and the second stage filter PPF2 generates high-accuracy 4-phase signals within a frequency band, Fc2=3.5 GHz.

Figure 9:
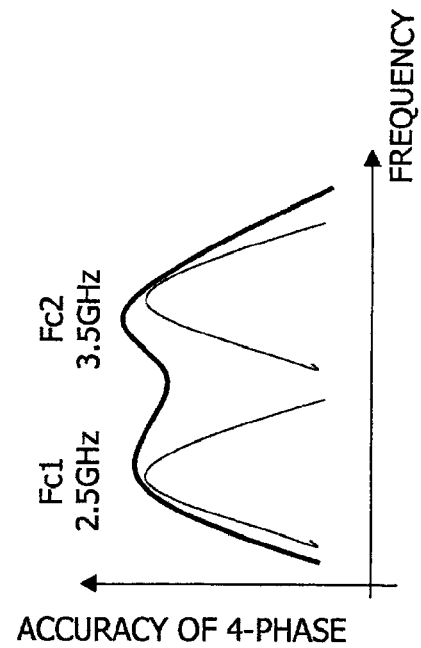
FIG. 9 illustrates the frequency characteristic in FIG. 8.

FIG. 9 is a drawing for illustrating the frequency characteristic with regard to FIG. 8. The horizontal axis represents the frequency, and the vertical axis represents the accuracy of the 4-phase outputs. As illustrated in FIG. 9, since, in a poly-phase filter of 2-stage configuration, high-accuracy 4-phase signals are generated at cut-off frequencies Fc1, Fc2 of the stages, the frequency band thereof is broadened from Fc1 to Fc2. However, in a poly-phase filter, attenuation amount of signal becomes large as the number of stages grows, and thus increasing stages is not practical. Hence, there is a limitation in broadening the frequency band merely by increasing stages.

It is preferred that the reception circuit with a single-side band mixer illustrated in FIG. 3 processes reception signal RF in a wide frequency band. On the other hand, as described above, a poly-phase filter generates high-accuracy 4-phase first local frequency signals LO(DMIX) only in the cut-off frequency band. Therefore, if the frequency band of the poly-phase filter is broadened, the frequency band of the single band mixer using the same is enabled to be broadened.

Figure 10:
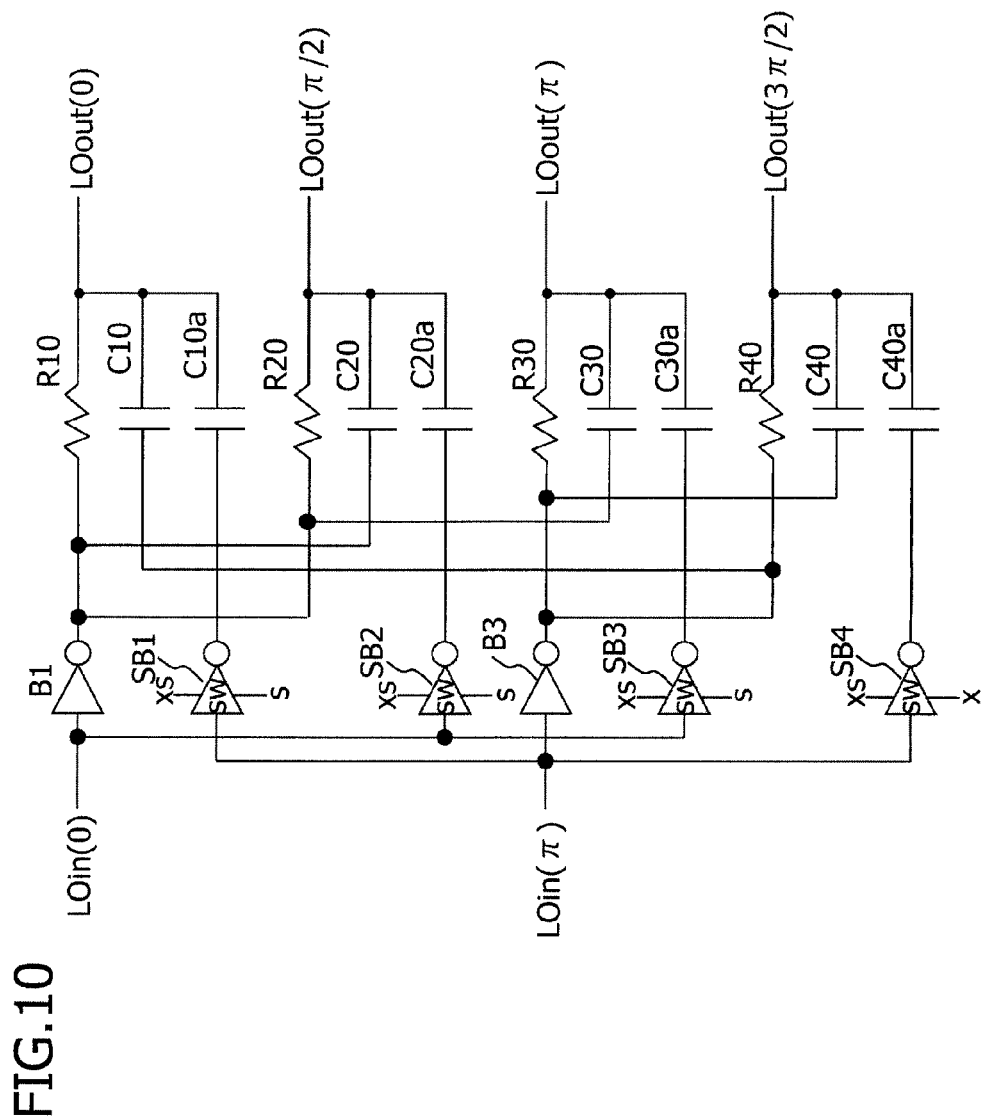
FIG. 10 is a circuit diagram of the poly-phase filter of an embodiment.

FIG. 10 is a circuit diagram of a poly-phase filter of the present embodiment. This example illustrates a single stage filter which takes in 2-phase input signals LOi, LOi_b and outputs 4-phase output signals LOout(0)-LOout(3$\pi$/2). Four filter units have the resistors R10-R40 of the same the resistance values, and the primary capacitors C10-C40 of the same capacitance values. Configuration described above is the same as FIG. 7.

In the embodiment of FIG. 10, four filter units further have secondary capacitors C10$a$-C40$a$ in parallel to the primary capacitors C10-C40. Then, 2-phase input signals LOin(0), LOin($\pi$) are provided, via the buffers B1, B2, to input (left-side) terminals of the resistors R10, R20. Also, in the secondary capacitor C10$a$, one terminal is connected to the output (right-side) terminal of the resistor R10, and the other terminal is provided with the input signal LOi_b via the switch buffer SB1. Similarly, in the secondary capacitor C20$a$, one terminal is connected to the output (right-side) terminal of the resistor R20, and the other terminal is provided with the input signal LOi via the switch buffer SB2. In the secondary capacitor C30$a$, one terminal is connected to the output (right-side) terminal of the resistor R30, and the other terminal is provided with the input signal LOi via the switch buffer SB3.

Finally, in the secondary capacitor C40a, one terminal is connected to the output (right-side) terminal of the resistor R40, and the other terminal is provided with the input signal LOi_b via the switch buffer SB4.

Figure 11:
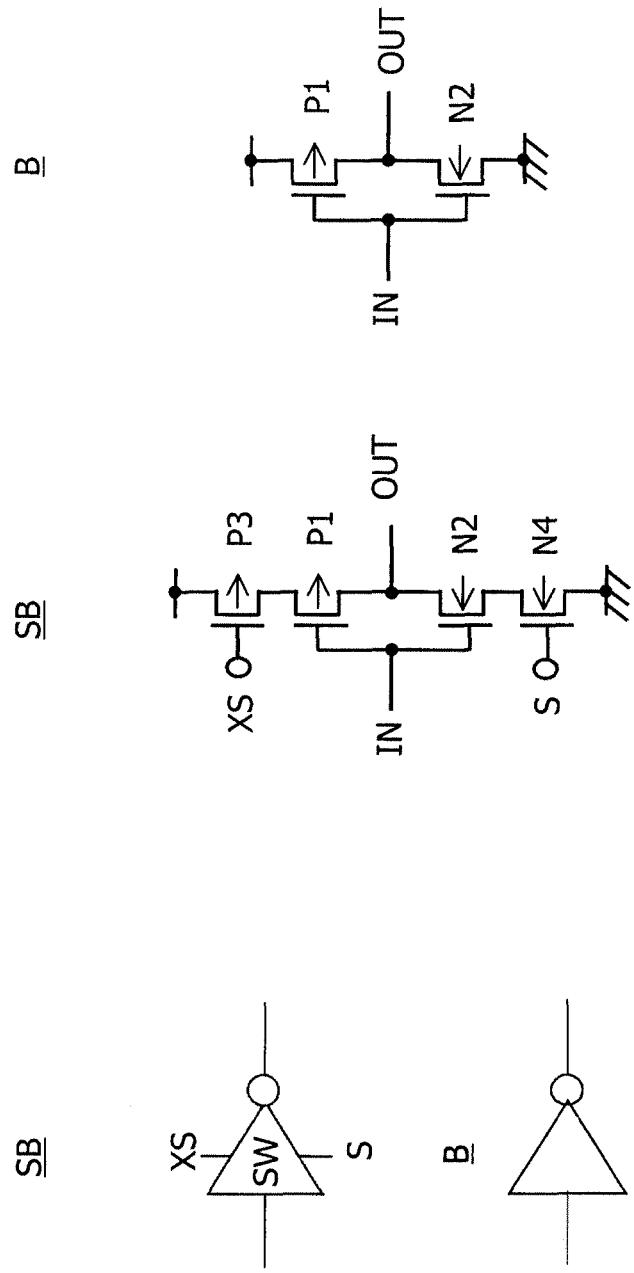
FIG. 11 illustrates circuit diagrams of a buffer and a switch buffer of the poly-phase filter of an embodiment.

FIG. 11 illustrates circuit diagrams of an input buffer and a switch buffer of a poly-phase filter of the present embodiment. A switch buffer SB includes an inverter circuit constituted by a P-channel transistor P1 and an N-channel transistor N1, and a P-channel transistor P3 and an N-channel transistor N4a which are controlled by switching signals XS,S having phases reverse from each other. Therefore, in the switch buffer SB, when the switching signals XS, S respectively turn to be H- and L-levels, the transistors P3, N4 turn to be OFF, thus becoming output high-impedance state (OFF state). Also, when the switching signals XS, S respectively turn to be L- and H-levels, the transistors P3, N4 turn to be ON, thus constituting a normal inverter circuit (ON state).

On the other hand, an input buffer B is an inverter circuit constituted by the transistors P1, N2. Here, the input buffer B may be the same circuit configuration as the switch buffer SB with the switching signals XS, S steadily being L- and H-levels, so that the input buffer B may be used as the inverter circuit. In that case, operations of buffer B and the switch buffer SB are equivalent and well balanced, which is rather preferable.

Backing to FIG. 10, the input signal LOi_b is input via the input buffer B3 and the switch buffer SB1 to both of the primary capacitor C10 and the secondary capacitor C10a. Therefore, when the switch buffer SB1 is in ON state (non-high-impedance state), the left-side terminal of the secondary capacitor C10a and the left-side terminal of the primary capacitor C10 are at the same signal state, thus substantially being short. As a result, the primary capacitor C10 and the secondary capacitor C10a are substantially same as parallelly connected configuration. On the other hand, when the switch buffer SB1 is in OFF state (high-impedance state), the secondary capacitor C10a is substantially non-existent.

That is, when the switch buffer SB1 is in ON state (non-high impedance state), the cut-off frequency Fc is such that, Fc=1/(2πR10*(C10+C10a)), while, when the switch buffer SB1 is in OFF state (high impedance state), the cut-off frequency Fc is such that Fc=1/(2πR10*C10).

Therefore, by adjusting the capacitance values of the primary capacitor C10 and the secondary capacitor C10a, the cut-off frequency of the poly-phase filter of FIG. 10 may be set at two preferable frequencies. As a result, by controlling operational frequency band of the single-stage poly-phase filter of FIG. 10 to be high and low bands through switching the switching signals XS, S, the operational frequency band may be substantially broadened.

Figure 12:
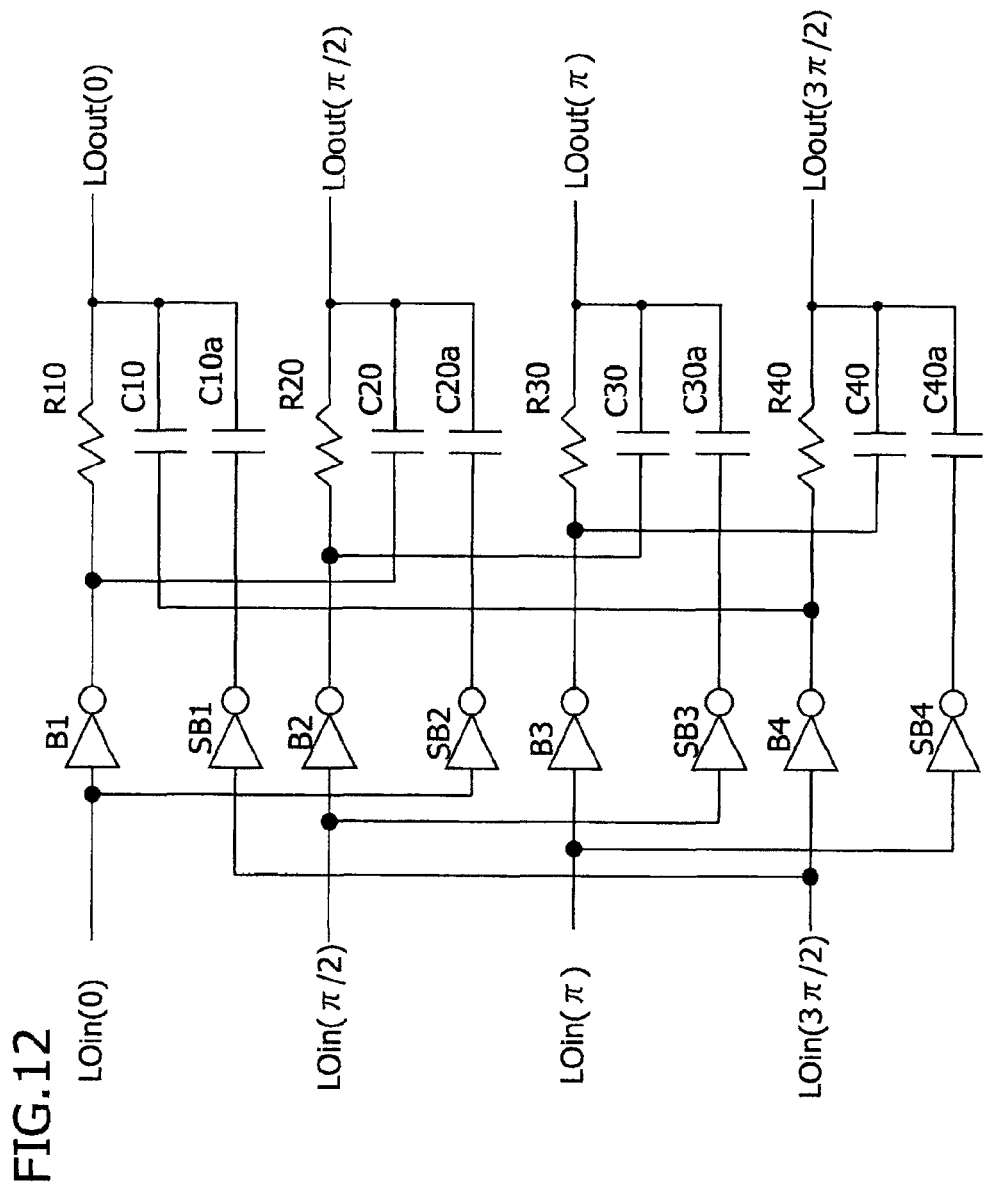
FIG. 12 is other circuit diagram of the poly-phase filter of the present embodiment.

FIG. 12 is another circuit diagram of a poly-phase filter of the present embodiment. In this example, 4-phase input signals LOin(0), LOin(π/2), LOin(π) and LOin(3 π/2) are input, and the input signals are respectively provided via the input buffers B1-B4 to the resistors R10-R40. Together with this, the input signals LOin(3π/2), LOin(0), LOin(π/2), and LOin(π) are respectively provided via the switch buffers SB1-SB4 to the secondary capacitors C10a-C40a. The manner of operations thereof is the same as in FIG. 10.

Furthermore, the poly-phase filter is applied to a case that a single input signal is provided via a single input buffer B to the input terminals of the resistors R10-R40. In that case, a single input signal is provided via the four switch buffers SB1-SB4 to the four secondary capacitors C10a-C40a.

In the poly-phase filters of FIG. 10 and FIG. 12, configurations are also possible such that, in addition to the secondary capacitors C10a-C40a and the switch buffers SB1-SB4, second secondary capacitors C10b-C40b and second switch buffers SB1b-SB4b(not illustrated) are configured in a similar manner, and that the switch buffers SB1-SB4 and the second switch buffers SB1b-SB4b are controlled by different switching signals. As a result, switching is enabled among the first cut-off frequency in the case of configuring the filter with the primary capacitor C10-C40, the second cut-off frequency in the case of configuring the filter with the primary capacitor and the first secondary capacitors C10a-C40a, the third cut-off frequency in the case of configuring the filter with the primary capacitor and the second secondary capacitors C10b-C40b, and the fourth cut-off frequency in the case of configuring the filter with the primary capacitor, the first and second secondary capacitors C10a-C40a, C10b-C40b. As a result, broader frequency band is obtained.

Figure 13:
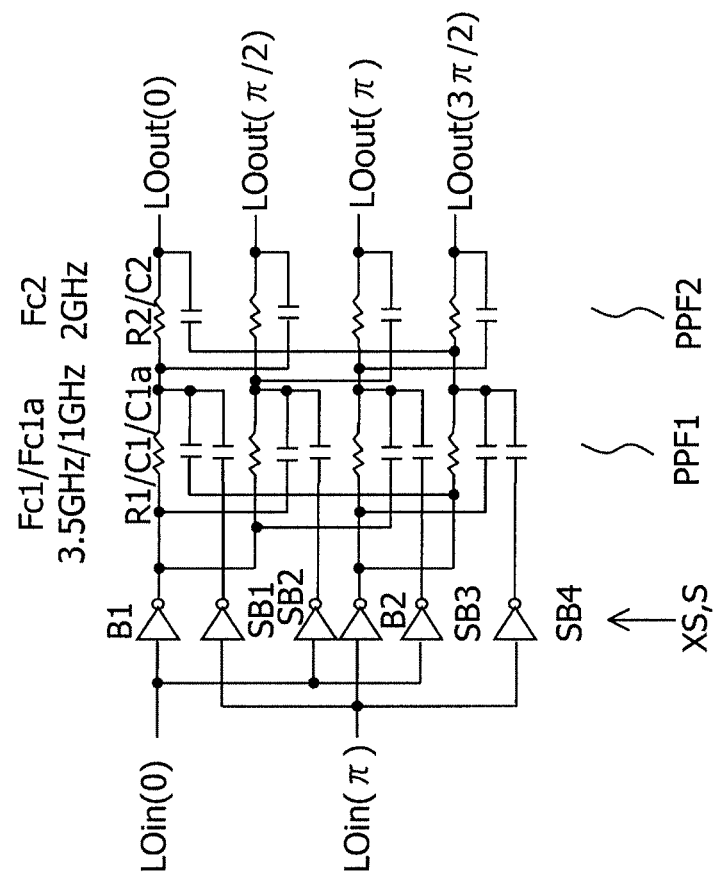
FIG. 13 is a circuit diagram of the poly-phase filter of an embodiment.

FIG. 13 is a circuit diagram of a poly-phase filter of the present embodiment. In this example, at the first stage of a 2-stage filter, the primary capacitor C1 and the secondary capacitor C1a are provided in parallel. That is, the configuration of the first stage poly-phase filter PPF1 is the same as FIG. 10, and the configuration of the second stage poly-phase filter PPF2 is the same as FIG. 7. At the four RC-filter units at the first stage, to which 2-phase input signals LOin(0), LOin (π) are input, the resistor R1, the primary capacitor C1, and the secondary capacitor C1a are provided, and at the four RC-filter units at the second stage, the resistor R2 and the capacitor C2 are provided. As briefly illustrated, the four filter units are assumed to be configured with the same resistors R1, R2, and the same capacitors C1, C1a, and C2. Also, to the switch buffers SB1-SB4, the switching signals XS, S are provided.

The cut-off frequency of the first stage poly-phase filter PPF1 turns to be high cut-off frequency Fc1 by the resistor R1 and the primary capacitor C1, when the switching signals XS, S are respectively H-, L-levels and the switch buffers SB1-SB4 are in high-impedance state, and, in a contrary, low cut-off frequency Fc1a by the primary capacitor C1, the secondary capacitor C1a, and the resistor R1, when the switching signals XS, S are respectively L-, H-levels and the switch buffers SB1-SB4 are in non-high-impedance state (conductive state). That is, as described as follows.

$$Fc1 = 1/2\pi R1 C1$$

$$Fc1a = 1/2\pi R1(C1+C1a)$$

Incidentally, Fc1=3.5 GHz, and Fc1a=1 GHz in the drawing are for illustrative purpose.

Further, the cut-off frequency Fc2 of the second-stage poly-phase filter PPF2 turns to be a frequency by the resistor R2 and the capacitor C2, such that, Fc2=1/2πR2C2. In the drawing, Fc2=2 GHz is described for illustrative purpose.

Figure 14:
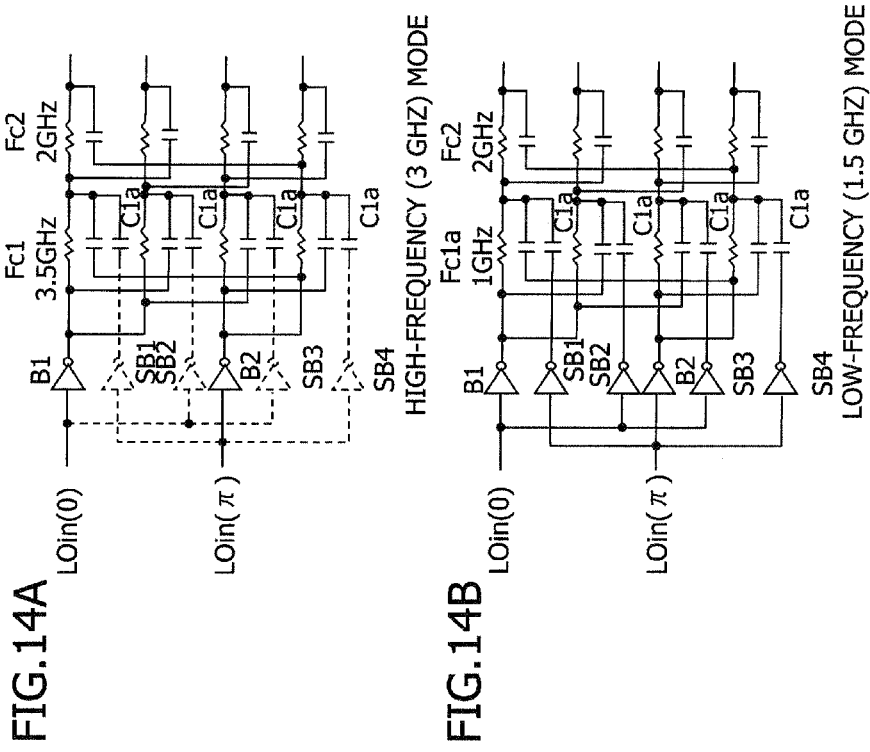
FIG. 14 illustrates cases of the poly-phase filter of FIG. 13 being used in a high-frequency mode and in a low-frequency mode.

FIG. 14 is a drawing for illustrating an example in which the poly-phase filter of FIG. 13 is used in a high-frequency mode and a low-frequency mode. In the case of FIG. 14A, the switching signals XS, S respectively turn to be H-, L-levels, and switch buffers SB1-SB4 are made to be in high-impedance state. As a result, as illustrated by a dashed-line in the drawing, the input signals LOin(0), LOin(π) are not provided to the secondary capacitor C1a. Therefore, the first-stage has a high cut-off frequency Fc1.

On the other hand, in the case of FIG. 14B, the switching signals XS,S respectively turn to be L,H-levels, and the switch buggers SB1-SB4 are made to be in non-high impedance state (conductive state). As a result, the input signals LOin(0), LOin(π) are provided to the secondary capacitor C1a. Therefore, the first-stage has a low cut-off frequency Fc1a.

Figure 15:
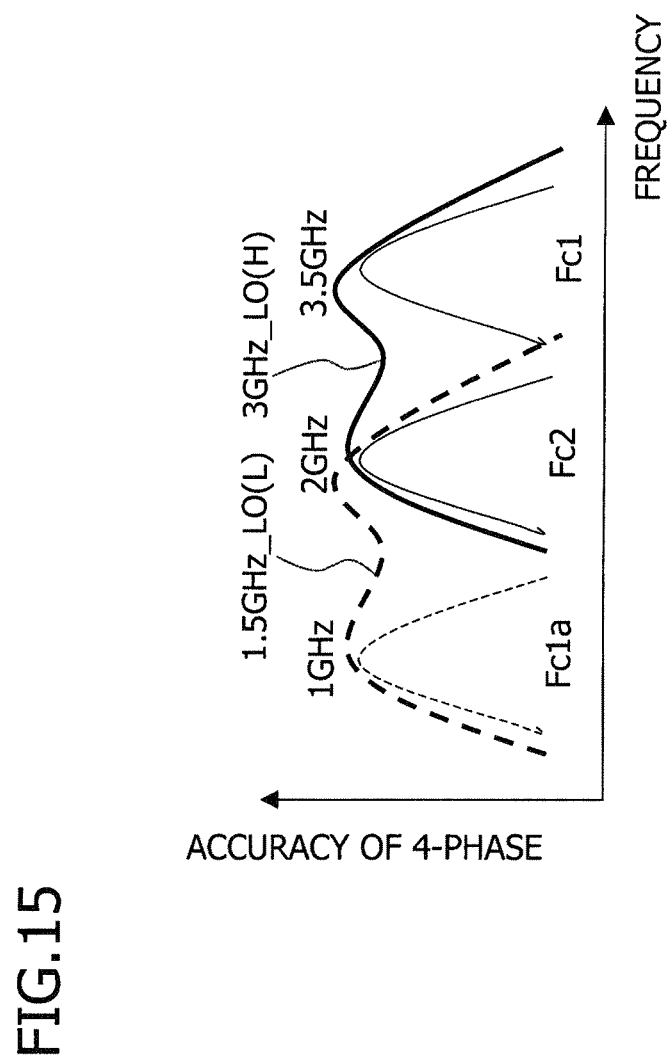
FIG. 15 illustrates the frequency characteristic of the poly-phase filter of FIG. 13.

FIG. 15 is a drawing for illustrating the frequency characteristic of the poly-phase filter of FIG. 13. The poly-phase filter in the case of FIG. 14A has a frequency characteristic obtained by combining the first-stage cut-off frequency, Fc1=3.5 GHz, and the second-stage cut-off frequency, Fc2=2 GHz. Therefore, a high frequency band LO(H) centering approximately on 3 GHz, as illustrated by a solid line in FIG. 15, is obtained. On the other hand, the poly-phase filter in the case of FIG. 14B has a frequency characteristic obtained by combining the first stage cut-off frequency, Fc1a=1 GHz, and the second stage cut-off frequency, Fc2=2 GHz. Therefore, a low frequency band LO(L) centering approximately on 1.5 GHz, as illustrated by a dashed-line in FIG. 15, is obtained.

As such, by controlling the switching signals XS, S, the frequency band of the poly-phase filter is switched to the high frequency band LO(H) and the low frequency band LO(L). Hence, by controlling the switching signal according to the frequency band of the input signal RF processed by a single-side band mixer, it is enabled to process the input signal RF in substantially broad frequency band.

Figure 16:
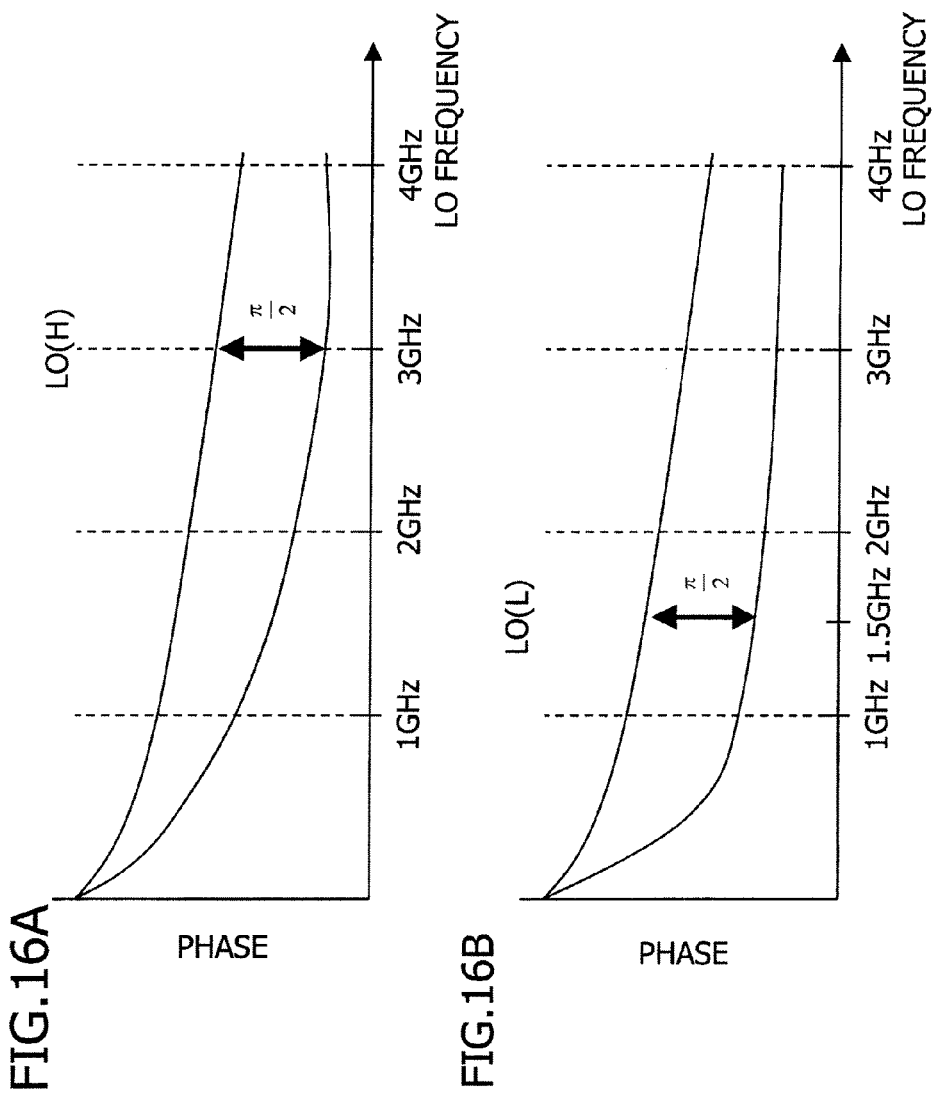
FIGS. 16A, 16B illustrate a simulation result of the present embodiment by the inventors.

FIG. 16 illustrates a simulation result of the present embodiment by the inventors. The inventors conducted a simulation of the poly-phase filter of FIG. 13, and examined the phase relations of the output signals in the cases of high frequency band LO(H) and low frequency band LO(L). In FIG. 16A, in which the horizontal axis represents the output frequency and the vertical axis represents the phase, two frequency-phase relations are illustrated. According thereto, it is observed that, when making the switching signals XS, S respectively H-, L-levels and making the switch buffers SB1-SB4 in high-impedance-state, phases of two output signals are shifted by 90 degrees ($\pi/2$) from each other with high accuracy in a band centering on a frequency of 3 GHz. On the other hand, as illustrated in FIG. 16B, it is observed that, when making the switching signals XS, S respectively L-, H-levels and making the switch buffers SB1-SB4 in non-high-impedance state, phases of two output signals are shifted by 90 degrees ($\pi/2$) from each other with high accuracy in a band centering on a frequency of 1.5 GHz.

Figure 17:
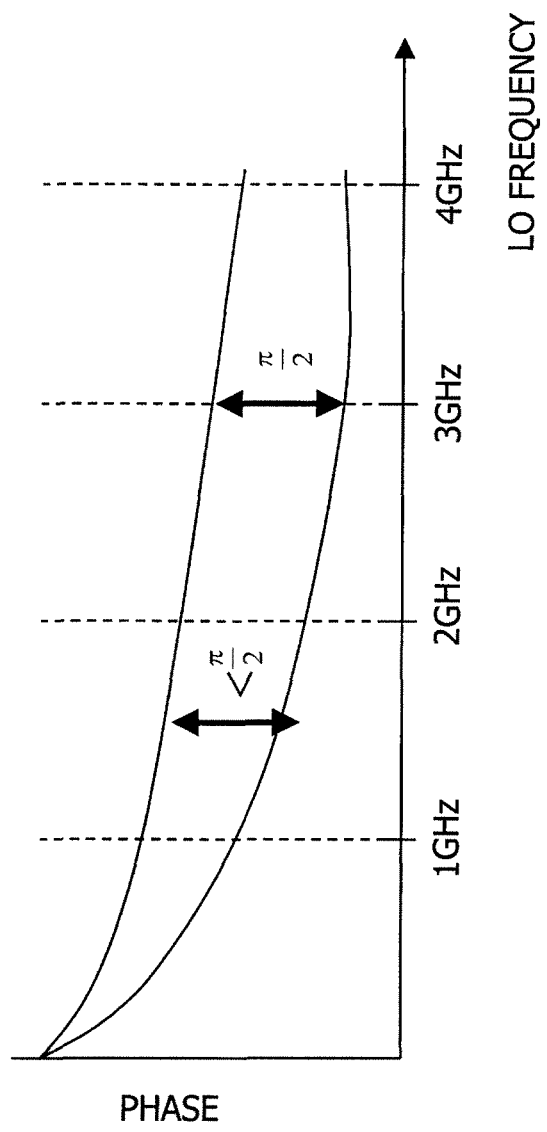
FIG. 17 is a circuit diagram of other poly-phase filter of an embodiment.

FIG. 17 illustrates a result of simulation conducted by the inventors with the poly-phase filter of FIG. 8. In this case, the phase difference between two output signals is 90 degrees with high accuracy in a band centering on a frequency of 3 GHz, however, the phase difference is less than 90 degree around 1.5 GHz. Consequently, this poly-phase filter is not preferably used in a 1.5 GHz band, and the frequency band is narrowed.

With respect to the poly-phase filter FIG. 13, it is preferable to set the resistors R1, R2 and the capacitors C1, C1a, and C2 so that three kinds of cut-off frequencies Fc1, Fc1a, and Fc2, such as Fc1=$1/2\pi R1C1$, Fc1a=$1/2\pi R1(C1+C1a)$, and Fc2=$1/2\pi R2C2$, satisfy a relation, Fc2−Fc1a=Fc1−Fc2. By this setting, the frequency characteristics in FIG. 15 are made to be such that the characteristics of the high frequency band LO(H) and the low frequency band LO(L) are in a symmetric manner with respect to frequency Fc2. Thereby, the poly-phase filter has equivalent characteristics in the high and low frequency-band modes.

Figure 18:
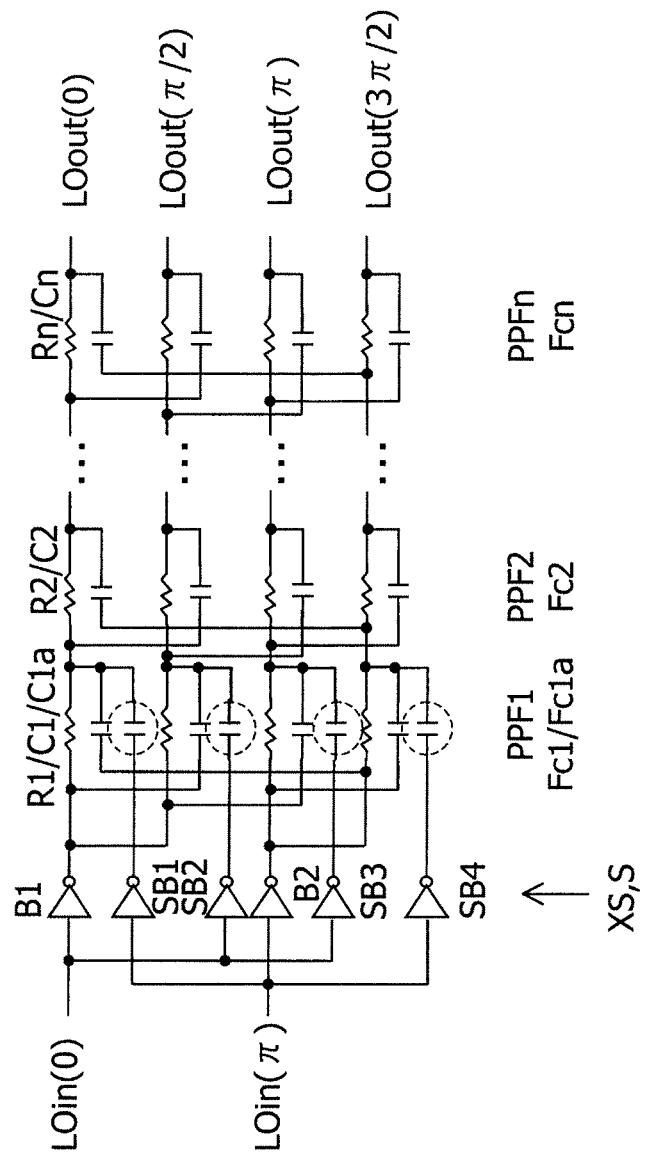
FIG. 18 is a circuit diagram of other poly-phase filter of an embodiment.

FIG. 18 is a circuit diagram of other poly-phase filter of the present embodiment. This poly-phase filter has, in addition to the first-stage filter PPF1, filters from the second-stage filter PPF2 to the Nth-stage filter PPFn, which constitutes N-stage configuration as the whole. The first-stage filter PPF1 is configured in the same manner as the first-stage filter PPF1 of FIG. 13, and the second- to Nth-stage filters PPF2-PPFn are configured in the same manner as the second-stage filter PPF2 of FIG. 13, except for the resistance values and the capacitance values differing.

Then, the first-stage poly-phase filter PPF1 alone has the primary capacitor C1 and the secondary capacitor C1a together with the resistor R1, and switches between the high cut-off frequency Fc1 and the low cut-off frequency Fc1a according to the switching signals XS, S. Also, the second- to Nth-stage filters PPF2-PPFn have different resistance values or capacitance values, and have the cut-off frequencies Fc2-Fcn which slightly differ from one another. Then, similarly to FIG. 13, 2-phase input signals are input, and 4-phase output signals are generated.

Figure 19:
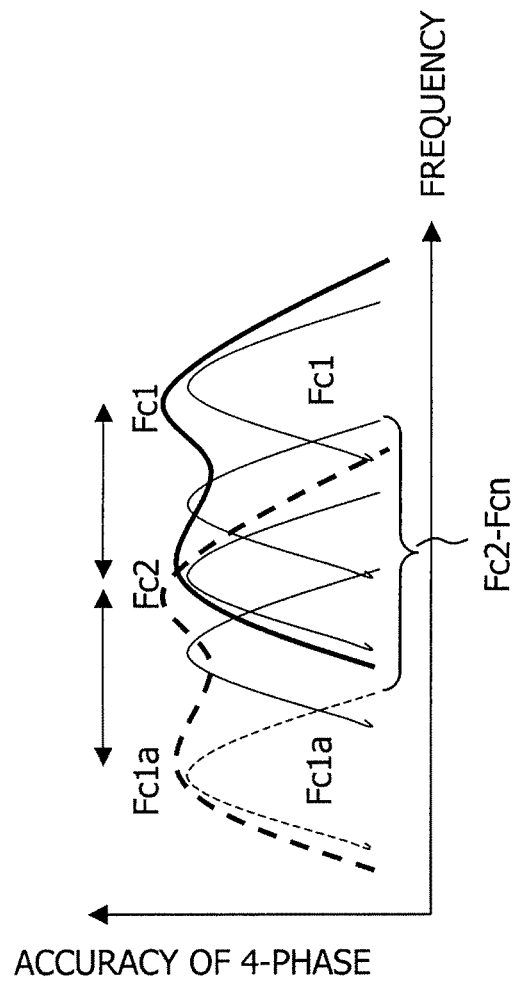
FIG. 19 illustrates the frequency characteristic of the poly-phase filter of FIG. 18.

FIG. 19 illustrates the frequency characteristic of the poly-phase filter of FIG. 18. The resistance values and the capacitance values of the filters are set so that two cut-off frequencies Fc1, Fc1a of the first-stage filter PPF1 are made to be respectively the maximum and the minimum frequencies, and the cut-off frequencies Fc2-Fcn of the second- to Nth-stage filters PPF2-PPFn are distributed in frequency region therebetween.

Two cut-off frequencies of the first-stage filter PPF1 are made to be such that Fc1=$1/2\pi R1C1$ and Fc1a=$1/2\pi R1(C1+C1a)$. Further, the average frequency of the cut-off frequencies Fc2-Fcn of the second- to Nth-stage filters is made to be such that Fo2=$(1/(2\pi R2C2)+ \ldots +1/(2\pi RnCn))/(n-1)$.

Then, by switching the first-stage filter according to the switching signal, it is enabled to switch the operational frequency band of the poly-phase filter, as in FIG. 19, between the high frequency band in a solid line and the low frequency band in a dashed line. In that case, it is preferable to set the resistance value and the capacitance value at each stage of the filters so that a relation Fc1−Fo2=Fo2−Fc1a is satisfied. By setting in such the manner, a poly-phase filter has the equivalent characteristics in the high-frequency-band mode and the low-frequency-band mode.

Figure 20:
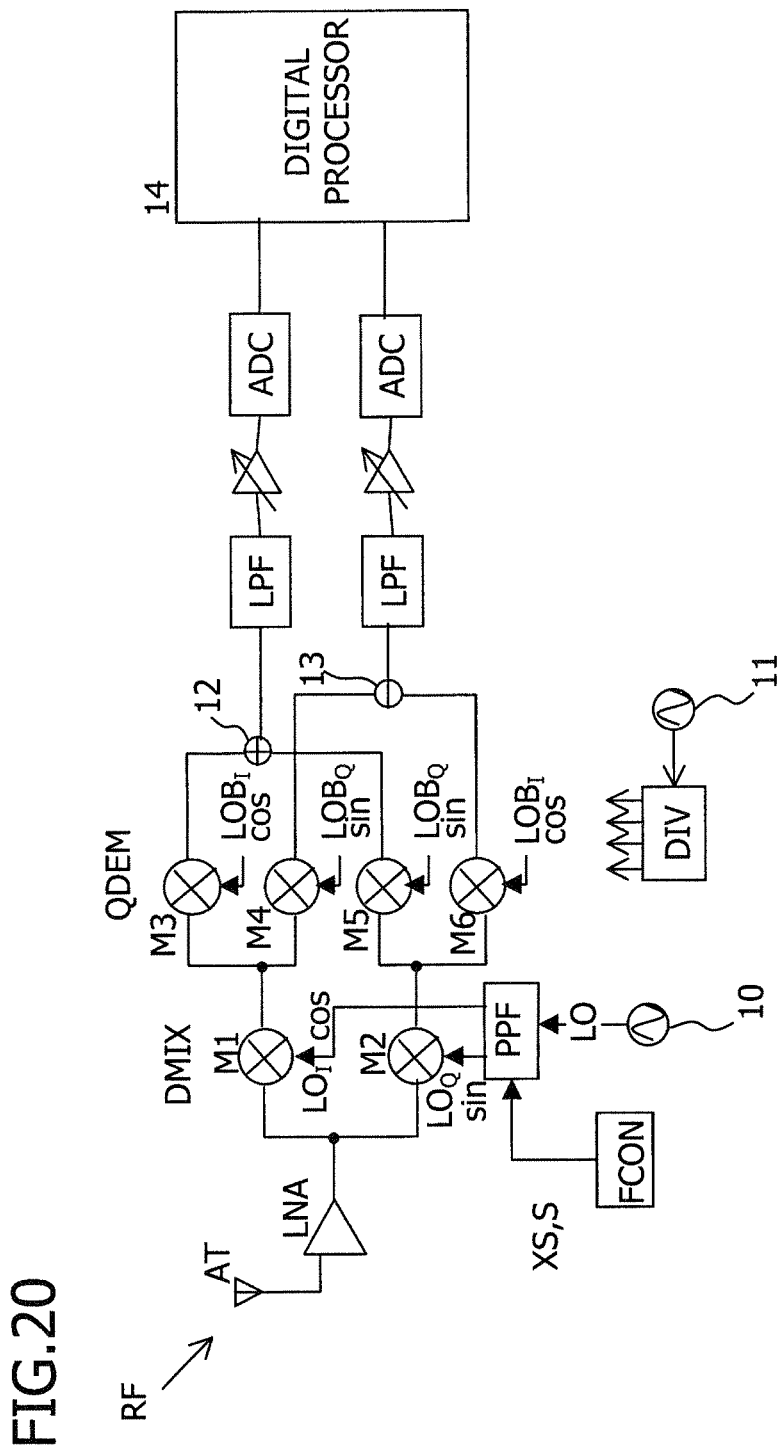
FIG. 20 illustrates a reception circuit of a single-side band mixer of an embodiment.

FIG. 20 is a drawing of the reception circuit of the single-side band mixer of the present embodiment. This reception circuit amplifies at the low-noise amplifier LNA the reception signal RF received by the antenna AT, and the amplified signal is multiplied by the first local frequency signals LOI, LOQ at the mixers M1, M2 of the downconverting mixer DMIX. These first local frequency signals LOI, LOQ are cosine wave and sine wave of which the phases are shifted by 90 degrees from each other. In the case of a differential configuration, the downconverting mixer DMIX has two mixers M1, M2 of the positive-phase side and two mixers M1, M2 of the opposite-phase (negative-phase) side. Here, the first local frequency signals LOI, LOQ of the positive-phase side and the first local frequency signals −LOI, −LOQ of the opposite-phase side are provided to the two corresponding mixers M1, M2.

The poly-phase filter PPF, having the same configuration as the above described embodiment, inputs signals (for example, single-phase, 2-phase, or 4-phase signals) generated by the oscillator 10, and generates the above 4-phase first local frequency signals LOI, LOQ, −LOI, and −LOQ. Then, a frequency control circuit FCON provides the switching signals XS, S to the poly-phase filter PPF and, by switching the switching signals XS, S, switches the frequency band thereof between high-side and low-side frequencies.

The quadrature-demodulating circuit QDEM at the subsequent-stage of the downconverting mixer DMIX has four mixers M3, M4, M5, and M6, the adder 12, and the subtractor 13. To the mixers M3, M6, the second local frequency signal LOBI is provided, and to the mixer M4, M5, the second local frequency signal LOBQ is provided. These signals LOBI, LOBQ are sine and cosine waves of which the phases are shifted by 90 degrees. Then, if the quadrature-demodulating circuit QDEM has a differential configuration, four mixers M3-M6 are configured on both the positive-phase side and the opposite-phase side, and the second local frequency signals LOBI, LOBQ are provided to the mixers on the positive-phase side, while the second local frequency signals −LOBI, −LOBQ are provided to the mixers on the opposite-phase side.

These 4-phase second local frequency signals are generated by the divider DIV. Also, the divider DIV is provided with a signal generated by the oscillator 11, and the divider generates the 4-phase signals.

Also, the frequency control circuit FCON switches the switching signals XS, S, according to the frequency band of the reception signal RF, so as to switch the frequency band between the high-frequency side and the low-frequency side.

The output of the adder 12 and the output of the subtractor 13 are provided to the digital processor 14 via the low pass filter LPF, the variable gain amplifier, and AD converter ADC. By the digital processor 14, modulation process or the like which are necessary for the reception circuit are performed.

The above described adder 12 may be configured with a subtractor, while, in that case, the subtractor 13 is configured with an adder.

Figure 21:
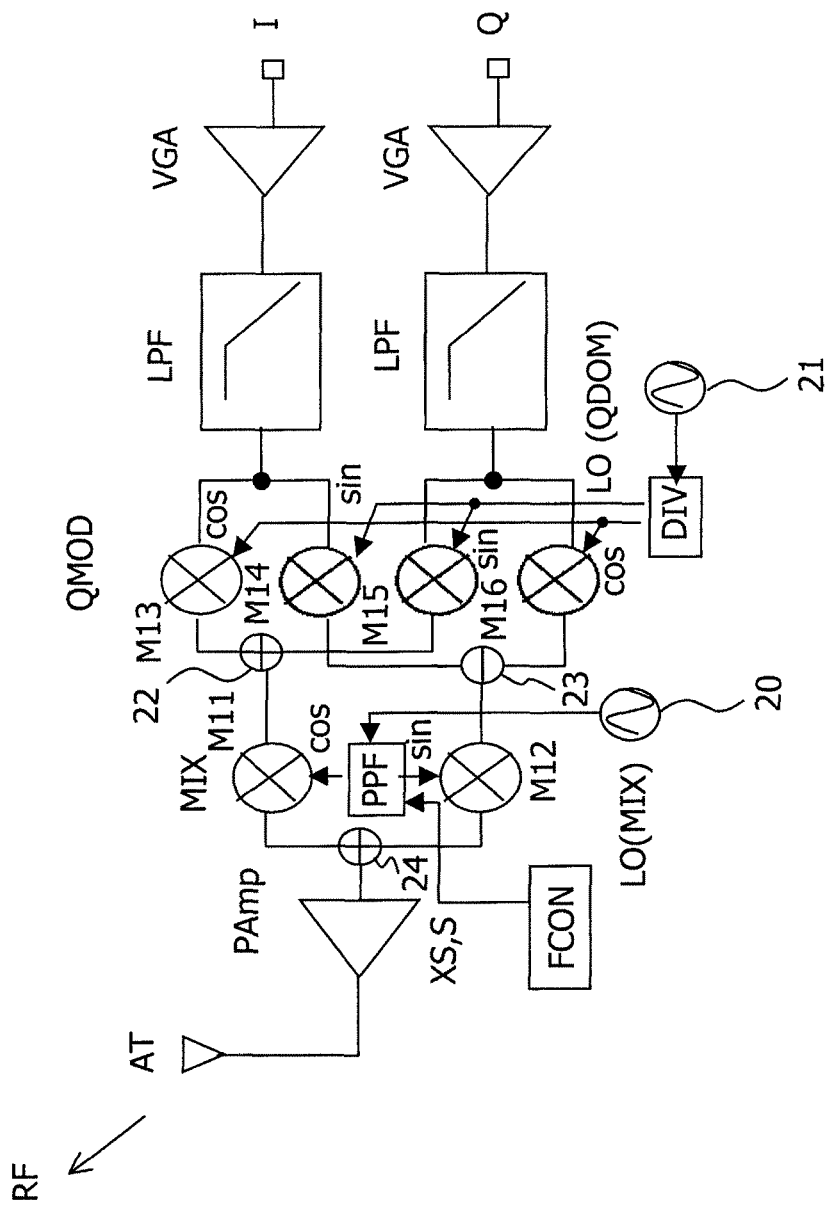
FIG. 21 illustrates a transmission circuit of the single-side band mixer of the present embodiment.

FIG. 21 is a drawing of a transmission circuit of the single-side band mixer of the present embodiment. I-signal components and Q-signal components are provided, via the variable gain amplifier VGA and the low pass filter LPF, to the quadrature-modulating circuit QMOD. The quadrature-modulating circuit QMOD has four mixers M13-M16, and is provided, as illustrated in the drawing, with two local frequency signals LO(QMOD)(sine wave and cosine wave), of which the phases are shifted by 90 degrees, generated by the divider DIV. Then, the adder 22, which adds outputs of the mixers M13, M15, and the subtractor 23, which subtracts the outputs of the mixers M14, M16, are configured. If the quadrature-modulating circuit QMOD has a differential configuration, four mixers M13-M16 are configured on the positive-phase side and the opposite-phase side, and two positive-phase and opposite-phase local frequency signals LO(QMOD) are provided. The above described adder 22 may be configured with a subtractor, while, in that case, the subtractor 23 is configured with an adder.

Further, the upconverting mixer MIX has two mixers M11, M12 which are provide with the two local frequency signals, of which the phases are shifted by 90 degrees, generated by the poly-phase filter PPF. In a differential configuration, the two mixers M11, M12 are configured on the positive-phase side and the opposite-phase side, and 4-phase local frequency signals from the poly-phase filter PPF are provided to the corresponding mixers.

Then, by the adder 24, outputs of the mixers M11, M12 are added, and, through a power amplifier PAMP, the output signal RF is transmitted from the antenna AT. From the signal to be transmitted from the antenna AT, a spurious signal is eliminated by the above single-side band mixer. There may be a case that the adder 24 is replaced with a subtractor.

Also in this transmission circuit, the frequency control circuit FCON switches the switching signals XS, S according to the frequency band of the reception signal RF, and thus switches the frequency band between the high-frequency side and the low-frequency side.

As described above, the poly-phase filter PPF of the present embodiment is enabled to generate 4-phase signals having phases shifted by 90 degrees in a wide frequency band with high accuracy. Also, the single-side band mixer, to which the poly-phase filter PPF is employed as generating means of the local frequency signal, is enabled to receive a reception signal or transmit a transmission signal in a wide frequency band.

The poly-phase filter PPF of the present embodiment and the single-side band mixer having the same may be used for, for example, a communication apparatus and the like.

What is claimed is:

1. A poly-phase filter inputting an input signal and outputting first-fourth 4-phase output signals, comprising:
   first-fourth resistors, each of which has an input terminal and an output terminal;
   a first primary capacitor provided between the output terminal of the first resistor and the input terminal of the fourth resistor;
   a second primary capacitor provided between the output terminal of the second resistor and the input terminal of the first resistor;
   a third primary capacitor provided between the output terminal of the third resistor and the input terminal of the second resistor;
   a fourth primary capacitor provided between the output terminal of the fourth resistor and the input terminal of the third resistor;
   an input buffer which inputs and outputs to the input terminals of the first-fourth resistors the input signal;
   a first secondary capacitor which is connected to the output terminal of the first resistor in parallel to the first primary capacitor;
   a first switch buffer which inputs and outputs to the first secondary capacitor the input signal being input to the input terminal of the fourth resistor;
   a second secondary capacitor which is connected to the output terminal of the second resistor in parallel to the second primary capacitor;
   a second switch buffer which inputs and outputs to the second secondary capacitor the input signal being input to the input terminal of the first resistor;
   a third secondary capacitor which is connected to the output terminal of the third resistor in parallel to the third primary capacitor;
   a third switch buffer which inputs and outputs to the third secondary capacitor the input signal being input to the input terminal of the second resistor;
   a fourth secondary capacitor which is connected to the output terminal of the fourth resistor in parallel to the fourth primary capacitor; and
   a fourth switch buffer which inputs and outputs to the fourth secondary capacitor the input signal being input to the input terminal of the third resistor, wherein
   the first-fourth output signals are respectively output from the output terminals of the first-fourth resistors, and
   the first-fourth switch buffers are controlled, in response to a switching signal, to be either output-high-impedance state or not.

2. The poly-phase filter according to claim 1, wherein
   the input signal includes first and second input signals of which phases are shifted from each other, and
   the input buffer includes a first input buffer which inputs and outputs to the input terminals of the first and the second resistors the first input signal, and a second input buffer which inputs and outputs to the input terminals of the third and the fourth resistors the second input signal.

3. The poly-phase filter according to claim 1, wherein
   the input signal includes first and second input signals of which phases are shifted from each other, and the input buffer includes the first-fourth input buffers which respectively input and output to the input terminals of the first-fourth resistors the first-fourth input signals.

4. The poly-phase filter according to claim 1, wherein a ratio of a driving capability of the input buffer to a driving capability of the first-fourth switch buffers coincides with a capacitance ratio of the primary capacitor to the secondary capacitor.

5. A reception-side single-band mixer comprising:
the poly-phase filter according to claim 1, which input a first local frequency signal as the input signal;
a downconverting mixer including a first mixer which multiplies a high-frequency input signal by the first output signal, the third output signal, or the first and the third output signals of the poly-phase filter, and a second mixer which multiplies the high-frequency input signal by the second output signal, the fourth output signal, or the second and fourth output signals of the poly-phase filter;
a quadrature-demodulating circuit which includes third and fourth mixers which respectively multiply outputs of the first and second mixers by a second local frequency signal, a first adder/subtractor which computes sum or difference of outputs of the third and fourth mixers, and outputs an I signal, fifth and sixth mixers which respectively multiply outputs of the first and second mixers by the second local frequency signal, and a second adder/subtractor which computes sum or difference of outputs of the fifth and sixth mixers, and outputs a Q signal.

6. The reception-side single-band mixer according to claim 5, further comprising a frequency-band controlling unit, which provides the switching signal to the first-fourth switch buffers according to reception frequency band, and controls the first-fourth switch buffers to be either the high-impedance state or not.

7. A transmission-side single-band mixer comprising:
a quadrature-modulating circuit which includes third and fourth mixers each multiplying an I signal by a second local frequency signal, fifth and sixth mixers each multiplying a Q signal by the second local frequency signal, a first adder/subtractor computing sum or difference of outputs of the third and fifth mixers, and a second adder/subtractor computing sum or difference of outputs of the fourth and sixth mixers,
the poly-phase filter according to claim 1, which inputs a first local frequency signal as the input signal,
an upconverting mixer which includes a first mixer multiplying an output signal of the first adder/subtractor by the first output signal, the third output signal, or the first and third output signals of the poly-phase filter, and a second mixer multiplying an output signal of the second adder/subtractor by the second output signal, the fourth output signal, or the second and fourth output signals.

8. The transmission-side single-band mixer according to claim 7, further comprising a frequency-band controlling unit which provides the switching signal to the first-fourth switch buffers according to a transmission frequency band, and controls the first-fourth switch buffers to be either the high-impedance state or not.

9. A poly-phase filter inputting an input signal and outputs 4-phase first-fourth output signals, comprising:
a first-stage filter unit circuit which inputs the input signal and outputs the 4-phase signals; and
a second-stage filter unit circuit which inputs the 4-phase signal output from the first-stage filter unit circuit,
wherein each of the first- and the second-stage filter unit circuits comprises:
first-fourth resistors each of which has an input terminal and an output terminal;
a first primary capacitor provided between the output terminal of the first resistor and the input terminal of the fourth resistor;
a second primary capacitor provided between the output terminal of the second resistor and the input terminal of the first resistor;
a third primary capacitor provided between the output terminal of the third resistor and the input terminal of the second resistor; and
a fourth primary capacitor provided between the output terminal of the fourth resistor and the input terminal of the third resistor,
wherein the first-stage filter unit circuit comprises:
an input buffer which inputs and outputs to the input terminals of the first-fourth resistors the input signal;
a first secondary capacitor which is connected to the output terminal of the first resistor in parallel to the first primary capacitor;
a first switch buffer inputs and outputs to the first secondary capacitor the input signal being input to the input terminal of the fourth resistor;
a second secondary capacitor which is connected to the output terminal of the second resistor in parallel to the second primary capacitor;
a second switch buffer which inputs and outputs to the second secondary capacitor the input signal being input to the input terminal of the first resistor;
a third secondary capacitor which is connected to the output terminal of the third resistor in parallel to the third primary capacitor;
a third switch buffer which inputs and outputs to the third secondary capacitor the input signal being input to the input terminal of the second resistor;
a fourth secondary capacitor which is connected to the output terminal of the fourth resistor in parallel to the fourth primary capacitor; and
a fourth switch buffer which inputs and outputs to the fourth secondary capacitor the input signal being input to the input terminal of the third resistor,
wherein the first-fourth output signals are respectively output from the output terminals of the first-fourth resistors of the second-stage filter unit circuit, and
the first-fourth switch buffers are controlled, in response to a switching signal, to be either output high-impedance state or not.

10. The poly-phase filter according to claim 9, wherein capacitances of the primary capacitor of the first-stage filter unit circuit and the secondary capacitor are set so that a difference between a first frequency corresponding to the resistor and the primary capacitor of the first-stage filter unit circuit and a second frequency corresponding to the resistor and the primary capacitor of the second-stage filter unit circuit coincides with a difference between a third frequency corresponding to the resistor, the primary capacitor, and the secondary capacitor of the first-stage filter unit circuit and the second frequency.

11. The poly-phase filter according to claim 9, further comprising the third-Nth stage filter unit circuits being serially connected to an output of the second-stage filter unit circuit, wherein the first-fourth output signals are respectively output from output terminals of the first-fourth resistors of the Nth-stage filter unit circuit, and capacitances of the primary capacitor of the first-stage filter unit circuit and the secondary capacitor are set so that a difference between a first frequency corresponding to the resistor and the primary capacitor of the first-stage filter unit circuit and the average frequency of the second-Nth frequencies corresponding to the resistors and the primary capacitors of the second-Nth filter unit circuits coincides with a difference between a third frequency corresponding to the resistor, the primary capacitor, and the secondary capacitor of the first-stage filter unit circuit and the average frequency.

12. A poly-phase filter inputting first and second input signals, of which phases are shifted from each other, and outputting first-fourth 4-phase output signals, comprising:

first-fourth resistors, each of which includes an input terminal and an output terminal;

a first primary capacitor provided between the output terminal of the first resistor and the input terminal of the fourth resistor;

a second primary capacitor provided between the output terminal of the second resistor and the input terminal of the first resistor;

a third primary capacitor provided between the output terminal of the third resistor and the input terminal of the second resistor;

a fourth primary capacitor provided between the output terminal of the fourth resistor and the input terminal of the third resistor;

a first input buffer which inputs and outputs to the input terminals of the first and second resistors the first input signal;

a second input buffer which inputs and outputs to the input terminals of the third and fourth resistors the second input signal;

a first secondary capacitor which is connected to the output terminal of the first resistor in parallel to the first primary capacitor;

a first switch buffer which inputs and outputs to the first secondary capacitor the second input signal;

a second secondary capacitor which is connected to the output terminal of the second resistor in parallel to the second primary capacitor;

a second switch buffer which inputs and outputs to the second secondary capacitor the first input signal;

a third secondary capacitor which is connected to the output terminal of the third resistor in parallel to the third primary capacitor;

a third switch buffer which inputs and outputs to the third secondary capacitor the first input signal;

a fourth secondary capacitor which is connected to the output terminal of the fourth resistor in parallel to the fourth primary capacitor; and a fourth switch buffer which inputs and outputs to the fourth secondary capacitor the second input signal, wherein the first-fourth output signals are respectively output from the output terminals of the first-fourth resistors, and the first-fourth switch buffers are controlled, in response to a switching signal, to be either output high-impedance state or not.

13. A poly-phase filter inputting first-fourth input signals, of which phases are shifted from one another, and outputting first-fourth 4-phase output signals, comprising:

first-fourth resistors, each of which has an input terminal and an output terminal;

a first primary capacitor provided between the output terminal of the first resistor and the input terminal of the fourth resistor;

a second primary capacitor provided between the output terminal of the second resistor and the input terminal of the first resistor;

a third primary capacitor provided between the output terminal of the third resistor and the input terminal of the second resistor;

a fourth primary capacitor provided between the output terminal of the fourth resistor and the input terminal of the third resistor;

first-fourth input buffers which respectively input and output to the input terminals of the first-fourth resistors the first-fourth input signals;

a first secondary capacitor which is connected to the output terminal of the first resistor in parallel to the first primary capacitor;

a first switch buffer which inputs and outputs to the first secondary capacitor the fourth input signal;

a second secondary capacitor which is connected to the output terminal of the second resistor in parallel to the second primary capacitor;

a second switch buffer which inputs and outputs to the second secondary capacitor the first input signal;

a third secondary capacitor which is connected to the output terminal of the third resistor in parallel to the third primary capacitor;

a third switch buffer which inputs and outputs to the third secondary capacitor the second input signal;

a fourth secondary capacitor which is connected to the output terminal of the fourth resistor in parallel to the fourth primary capacitor; and a fourth switch buffer which inputs and outputs to the fourth secondary capacitor the third input signal, wherein the first-fourth output signals are respectively output from the output terminals of the first-fourth resistors, and the first-fourth switch buffers are controlled, in response to a switching signal, to be either output-high-impedance state or not.

* * * * *